United States Patent [19]

Goetz

[11] 3,962,341

[45] June 8, 1976

[54] PRODUCTION OF PIPERITENONE

[75] Inventor: Norbert Goetz, Bobenheim-Roxheim, Germany

[73] Assignee: BASF Aktiengesellschaft, Ludwigshafen (Rhine), Germany

[22] Filed: Feb. 4, 1974

[21] Appl. No.: 439,053

[30] Foreign Application Priority Data

Feb. 6, 1973 Germany.............................. 2305628

[52] U.S. Cl............................................. 260/586 C
[51] Int. Cl.$^2$....................................... C07C 45/00
[58] Field of Search ................................ 260/586 C

[56] References Cited
UNITED STATES PATENTS 3,238,261   3/1966   Beereboom..................... 260/586 C
3,592,856   7/1971   Offenhauer et aal. ....... 260/586 C X

OTHER PUBLICATIONS

Fischer et al., "Berichte," vol. 68, pp. 1726–1734, (1935).

Fischer et al., "Justis Liebig Arm.," vol. 494, pp. 263–271, (1932).

Mazarov et al., "Chem. Abst," vol. 52, p. 12792h (1958).

Conia et al., "Comp. Rend," vol. 250, pp. 356–358, (1960).

Wiemann et al., "Comp. Rend," vol. 253, pp. 1109–1110, (1961).

*Primary Examiner*—Norman Morgenstern
*Attorney, Agent, or Firm*—Johnston, Keil, Thompson & Shurtleff

[57] ABSTRACT

A process for the production of piperitenone by heating 3,3-dimethylacrolein in the presence of an acid. Piperitenone is a valuable intermediate for the synthesis of menthol which is much sought after for cosmetic and pharmaceutical purposes.

10 Claims, No Drawings

PRODUCTION OF PIPERITENONE

The present invention relates to a process for the production of piperitenone, which is of importance as a precursor for the production of menthol, by heating 3,3-dimethylacrolein in the presence of an acid in the liquid phase.

The monocyclic monoterpene alcohol menthol occurs preferentially in the l-form as the principal constituent in peppermint oil which for that reason is the best starting material for the recovery of natural l-menthol. Several methods of producing l-menthol and dl-menthol semisynthetically start from ketones or unsaturated alcohols of the p-menthane series and by hydrogenation of menthones, menthenones, menthadienones, menthenols or menthadienols result in the desired product (cf. Gildemeister, Hoffman, "Die aetherischen Oele", Volume IIIb, pages 26 to 35, 1962). In addition to these syntheses there are two other interesting methods using natural substances as starting material; in one menthol is produced via isopulegol (p-menthen-8(9)-ol-3) starting from citronellal and in the other via piperitenol (p-menthadien-1,4(8)-ol-3) starting from α-pinene.

Difficulties which may arise in providing ethereal oils would appear to make it desirable to produce menthol from readily and constantly available starting materials. Conventional industrial syntheses of dl-menthol usually start from thymol. Since in the catalytic hydrogenation of thymol the desired dl-menthol is obtained in admixture with several stereoisomeric menthols, expensive purification of the dl-menthol by separation of the malodorous stereoisomeric alcohols or by rearrangement of the same into dl-menthol is necessary (cf. Gildemeister, loc. cit., pages 31 to 32).

It is therefore an object of the invention to provide a process by means of which there may be obtained from readily accessible starting materials in a simple manner menthol precursors from which dl-menthol can be prepared and isolated in a more economical manner than hitherto.

We have now found that surprisingly piperitenone can be prepared in a simple manner and in good yields by heating 3,3dimethylacrolein in the liquid phase in the presence of from 0.005 to 5% by weight and preferably from 0.01 to 1% by weight (based on the reaction mixture, i.e. dimethylacrolein and any solvent) of an acid having a pK value of 1 or more than 1 or in the presence of from 0.0005 to 0.05% by weight and preferably from 0.001 to 0.01% by weight (based on the reaction mixture) of an acid having a pK value of less than 1 at a temperature of from 165° to 350°C and preferably from 170° to 300°C.

3,3-dimethylacrolein used as starting material can be obtained fairly easily by reaction of isobutylene and formaldehyde followed by dehydrogenation of the 3-methyl-3-buten-1-ol obtained in this reaction.

Since both dimethylacrolein and piperitenone are sensitive to acid, particularly suitable catalysts for this reaction are weak acids, i.e. acids having a pK value of 1 or more than 1. Acids having a pK value of from 1 to 6 are preferred. Examples of preferred acids having a pK value of from 1 to 6 are formic acid, acetic acid, propionic acid, butyric acid, acrylic acid, dimethylacrylic acid, oxalic acid, malonic acid, succinic acid, maleic acid, adipic acid and benzoic acid, formic acid being particularly preferred. The acids in question are for the most part unsubstituted organic monocarboxylic or dicarboxylic acids of one to seven carbon atoms.

Examples of suitable strong acids having a pK value of 1 or less than 1 are p-toluenesulfonic acid, phosphoric acid and sulfuric acid.

In practice a reaction mixture is used to which such an amount of acid has been added that one of the commercial pH indicators when dipped into the reaction mixture containing the acid indicates a pH of from about 1 to 6 and preferably from 2 to 5.

The reaction may be carried out in the absence or presence of a solvent which is inert under the reaction conditions.

Aliphatic and aromatic hydrocarbons such as pentane, hexane, cyclohexane, heptane, benzene, toluene and xylene, ethers such as tetrahydrofuran and dioxane, and polar solvents such as 1,2-dimethoxyethane and dimethyl sulfoxide are suitable as solvents. The solvent is used in an amount which is one to five times the weight of the sum of the reaction components. The process may be carried out batchwise in a stirred vessel or shaker autoclave or continuously in a reactor or cascade of reactors.

The process of the invention may be carried out at a pressure of up to 250 atmospheres. In all cases the reaction conditions are so chosen that the reaction is carried out in liquid phase.

The reaction period for the reaction according to the invention is from 5 minutes to 10 hours and preferably from 15 minutes to 5 hours depending on the reaction temperature and the catalyst used.

The reaction mixture is worked up by fractional distillation.

Piperitenone (p-methadien-1,4(8)-one-3) prepared by the process according to the invention may be hydrogenated in a simple manner to menthol either in two stages via menthone as intermediate or in a single stage using a conventional hydrogenation catalyst such as a palladium, nickel or copper catalyst; menthol is much sought after for cosmetic and pharmaceutical purposes. Isolation of pure dl-menthol from piperitenone obtained by the process of the invention is much simpler than the isolation of dl-menthol from the hydrogenation products of thymol because fewer optical isomers are formed in the hydrogenation of piperitenone than in the hydrogenation of the aromatic thymol.

The invention is further illustrated by the following Examples in which parts are by weight.

EXAMPLE 1

A mixture of 200 parts of 3,3-dimethylacrolein, 600 parts of tetrahydrofuran and 1 part of formic acid is heated for 2 hours at a pressure of 120 atmospheres and a temperature of 280°C in an autoclave. The reaction product is worked up by distillation. 106 parts of piperitenone is obtained having a boiling point of 120° to 122°C at 14 mm Hg. The yield is 83% of theory at a conversion of 72%.

EXAMPLE 2

200 parts of 3,3-dimethylacrolein dissolved in 600 parts of pentane is heated with 5 parts of formic acid for 5 hours at a pressure of 90 atmospheres and a temperature of 230°C. After working up the reaction product 86.5 parts of piperitenone is obtained. The yield is 87% of theory at a conversion of 56%.

EXAMPLE 3

A mixture of 200 parts of 3,3-dimethylacrolein and 600 parts of tetrahydrofuran is heated with 0.008 part of p-toluenesulfonic acid in an autoclave for three hours at a pressure of 50 atmospheres and a temperature of 210°C. The reaction product is worked up by distillation. 72.5 parts of piperitenone is obtained. The yield is 78% of theory at a conversion of 52%.

I claim:

1. A process for the production of piperitenone wherein 3,3-dimethylacrolein is heated in the presence of from 0.005 to 5% by weight, based on the reaction mixture, of an unsubstituted organic monocarboxylic or dicarboxylic acid having 1–7 carbon atoms having a pK value of 1–6 or in the presence of from 0.0005 to 0.05% by weight, based on the reaction mixture, of a strong acid having a pK value of less than 1 in the liquid phase at a temperature of from 165° to 350°C.

2. A process as claimed in claim 1, wherein the said temperature is from 170° to 300°C.

3. A process as claimed in claim 1 carried out in the presence of one of said carboxylic acids having a pK value of from 1 to 6.

4. A process as claimed in claim 1, wherein 3,3-dimethylacrolein is heated in the presence of from 0.01 to 1% by weight, based on the reaction mixture, of one of said carboxylic acids having a pK value of 1.6.

5. A process as claimed in claim 1, wherein 3,3-dimethylacrolein is heated in the presence of from 0.001 to 0.01% by weight, based on the reaction mixture, of said strong acid having a pK value of less than 1.

6. A process as claimed in claim 1 carried out in the presence of a solvent.

7. A process for the production of piperitenone wherein 3,3-dimethylacrolein is heated in the presence of 0.005 to 5% by weight, based on the reaction mixture, of formic acid in the liquid phase at a temperature of from 165° to 350°C.

8. A process for the production of piperitenone wherein 3,3-dimethylacrolein is heated in the presence of 0.0005 to 0.05% by weight, based on the reaction mixture, of p-toluenesulfonic acid in the liquid phase at a temperature of from 165° to 350°C.

9. A process for the production of piperitone wherein 3,3-dimethylacrolein is heated in the liquid phase at 165–350°C in the presence of from 0.005 to 5% by weight, based on the reaction mixture, of an acid selected from the group consisting of formic acid, acetic acid, propionic acid, butyric acid, acrylic acid, dimethylacrylic acid, oxalic acid, malonic acid, succinic acid, maleic acid, adipic acid and benzoic acid.

10. A process for the production of piperitone wherein 3,3-dimethylacrolein is heated in the liquid phase at 165°–350°C in the presence of 0.0005 to 0.05% by weight, based on the reaction mixture, of an acid consisting of the group consisting of p-toluenesulfonic acid, phosphoric acid and sulfuric acid.

* * * * *